United States Patent [19]
Suenaga et al.

[11] 3,940,480
[45] Feb. 24, 1976

[54] PROCESS FOR PRODUCTION OF STABILIZED POWDERY SECRETIN PREPARATION BY LYOPHILIZATION

[75] Inventors: Eiichi Suenaga, Kunitachi; Shinro Tachibana, Narashino; Nagayasu Sato, Machida, all of Japan

[73] Assignee: Eisai Co., Ltd., Tokyo, Japan

[22] Filed: Apr. 26, 1973

[21] Appl. No.: 354,883

[30] Foreign Application Priority Data
May 8, 1972 Japan.............................. 47-44566

[52] U.S. Cl. .............................................. 424/177
[51] Int. Cl.² ........................................ A61K 37/00
[58] Field of Search .................................... 424/177

[56] References Cited
OTHER PUBLICATIONS

The Merck Index, 8th Ed., Merck & Co., Inc. Rahway, N.J., 1968, p. 939.

Primary Examiner—Jerome D. Goldberg
Attorney, Agent, or Firm—Wenderoth, Lind & Ponack

[57] ABSTRACT

Stabilized powdery secretin preparation wherein secretin is carried on an adequate amount of alanine serving as excipient and weighing material, which is produced by lyophilization of an aqueous solution of secretin in the presence of alanine, the product being useful for therapeutic treatment of diseases and for diagnosis of disorders in digestive tracts such as pancreas and gallbladder.

5 Claims, No Drawings

PROCESS FOR PRODUCTION OF STABILIZED POWDERY SECRETIN PREPARATION BY LYOPHILIZATION

This invention relates to a stabilized powdery secretin preparation and a process for the production thereof. More particularly, the invention relates to a stabilized powdery secretin preparation useful for therapeutic treatment, wherein the secretin is carried on an adequate amount of alanine serving as excipient and weighing material, and a process for the production thereof by lyophilization of an aqueous solution of secretin in the presence of the alanine.

Secretin is one of the hormones present in digestive tracts and capable of stimulating excretion of enzyme-free pancreatic juice from pancreas and inhibiting gastrine-stimulated gastric secretion. Secretin is therefore useful for therapeutic treatment of diseases in digestive tracts and for diagnosis of disorders thereof.

Secretin as is known is so unstable that it gradually loses its hormone activity even if kept at a low temperature such as −20°C. Addition of cysteine hydrochloride to secretin was proposed in order to improve its temperature stability and a certain increase in its stability was thus attained. It was found however that the stabilized secretin preparation is still unstable and cannot stand for a prolonged period of storage at room temperature. It is thus necessary to keep the preparation in a refrigerator.

Generally, lyophilization is often utilized for recovery of a substance in a powdery form from its aqueous solution where the substance is unstable under thermal treatment.

Where recovery of a medical substance from its aqueous solution is attempted, which medical substance is to be administered every in such minute amounts as a level of a few milligrams to a few micrograms, which can scarcely be identified with the naked eye, it is apparent that an immediate application of lyophilization procedure to said aqueous solution in the absence of carrier is inadvisable, because the resulting finely divided solid substance is liable to scatter in the wind under suction, especially towards the end of the lyophilization procedure. Scattering may also occur in the event of an accident that might occur in handling or transportation of said dry substance.

Such a difficulty as abovementioned may be avoided, if a lyophilization procedure is carried out with an aqueous solution of such a substance in the presence of a carrier which, when the operation is over, serves as a weighing material and excipient of the recovered substance, so that a minute amount of the recovered active substance is carried on a large amount of said carrier.

Selection of a suitable carrier for use in the lyophilization is desirably effected in view of the following three requisite conditions:

a. Carrier itself can easily be recovered from its aqueous solution by lyophilization.

b. Carrier is of a poor hygroscopicity and is yet of a good water-solubility.

Selection of a carrier of poor hygroscopicity is needed in order to obtain a lyophilization product in a bulky and flocculent mass with maintenance of its rapid and good water-solubility for a prolonged time of storage. This is for the reason that a dry preparation in such a bulky mass obtained by lyophilization in the presence of a hygroscopic carrier has generally a tendency of absorbing moisture to convert it into a dense, glassy conglomerate which is lacking in its original rapid and good water-solubility when stored in a humid atmosphere.

c. Carrier is chemically inactive toward the active agent to be recovered by lyophilization and should rather serve as a stabiliser for the active agent which, if any, is chemically unstable.

The above first condition (a) is satisfied by providing a substance which is capable of an instantaneous formation and growth of cryohydrate from its aqueous solution at a relatively high temperature below 0°C.

The second condition (b) is satisfied by providing a substance which, even though the same originally is of a good water-solubility, possesses a poor hygroscopicity.

Finally, the third condition (c) is satisfied by providing a substance suitably chosen by experimental routine works in consideration of the chemical characteristics of a particular active substance for which the lyophilization is being contemplated.

Saccharide derivatives such as dextrane, mannitol and the like have commonly been employed as the carrier, because they are first of all regarded as satisfying the abovementioned requisite conditions (a), (b) and (c). It is known by those skilled in the art that the individual aqueous solution of these carrier substances instantaneously forms cryohydrate at a relatively high temperature below 0°C., and furthermore most of the powdery substances obtained from their aqueous solutions by lyophilization are not hygroscopic and yet possess a good solubility in water sufficient to serve as an excipient and weighing material in the resulting preparations.

Now, the present inventors have effected several experiments by repeating the hitherto known lyophilization process with respect to various saccharide derivatives, in order to determine a commercially available carrier for the production of secretin preparation by lyophilization procedure. It was thus observed that saccharide derivatives usually regarded as a good carrier are lacking in the aforementioned third condition (c) of the requirements, because the saccharide derivatives have no property of fostering the chemical stability of secretin. Actually, secretin preparation obtained by lyophilization of its aqueous solution in the presence of mannitol as the carrier exhibited a gradual lowering of its hormone activity when the preparation was stored at room temperature for a certain period of time.

In view of the above stituation, we have extended our experiments over the other several compounds in order to find a compound which will satisfy the aforementioned three conditions required for a carrier for the production of secretin preparations. We have thus found that alanine is the substance having characteristics that satisfy all the abovementioned three conditions for a carrier to be used for the recovery of secretin by lyophilization from its aqueous solution.

It is to be understood that the term "alanine" used herein throughout the specification and claims is intended to mean both α-alanine and β-alanine. Although α-alanine may principally be employed in carrying out the process of this invention, β-alanine or a mixture of these two isomeric compounds may equally be used without difficulty.

The lyophilization of this invention is applicable to any of the aqueous solutions of both the natural and synthetic secretins obtained by the known methods.

Purified secretin, for example, may be used in the practice of this invention, which was obtained from an extract of the mucous membrane of small intestine of mammals such as in particular of cattle and pigs in accordance with the methods known by those skilled in the art.

In the practice of this invention, there is no particular limitation with respect to the quantity of alanine to be used. It has been found that use of alanine in a 2–10% aqueous solution is preferable. There is obtained a secretin preparation in a dry powdery form having a good appearance and containing 25 mg of alanine as weighing material and a minute amount of secretin, for example, by lyophilizing 0.5 ml of a secretin-containing 5% alanine aqueous solution held in an ampoule of 2 ml capacity.

Since secretin is stable at a pH ranging from 4 to 7, it is desirable to add, in addition to the alanine, a small quantity of a buffer substance to the aqueous solution of secretin to be subjected to lyophilization. The quantity of buffer substance added to the aqueous solution of secretin should be as small as possible, in such an amount of less than 0.05 m in each ampoule, in order to obtain a lyophilization product of good performance.

It has been found that the secretin preparation according to the invention, whether the same contains a buffer substance or not and regardless of the content and/or sort of said buffer, if any, withholds its original hormone activity of secretin for a considerably prolonged time of storage at room temperature. Accordingly, the process of this invention is of practical worth in commercial production of secretin preparations.

Following experiments will prove the beneficial technical effect achievable by the process of the invention.

Experiment 1

Choice of carrier:

We have confirmed that mannitol as a typical saccharide, and glycine, threonine, valine, α-alanine, β-alanine and citrulline as aminocarboxylic acid equally satisfy the conditions (a) and (b) amongst the conditions (a), (b) and (c) required for a carrier suitable for carrying out the lyophilization procedure in accordance with the present invention.

In the experiment, the effect of each of these carrier compounds on the stability of secretin was then estimated by periodically measuring the hormone activity of secretin contained in the individual secretin preparation which had been produced by the following lyophilization procedure.

Each aqueous solution of secretin was prepared which contained per ampoule 50 Crick, Harper and Raper units of secretin and 20 mg of the individual carrier. The ampoules were lyophilized in accordance with a conventional manner. The resulting lyophilization products were subjected to an accelerated test for damage at the elevated temperature of 45°C. and the remaining hormone activity of the secretin in each of the ampoules was periodically estimated in accordance with the method disclosed in Jap. J. Pharm., 21, 325–336 (1971). The results of the observations are listed in the following Table.

Table 1

| Carrier used | Remaining activity in C.H.R. Unit of secretin after | | | | |
|---|---|---|---|---|---|
| | 2 weeks | 4 weeks | 6 weeks | 12 weeks | 14 weeks |
| Mannitol | 58 | 67 | 54 | 30 | 38 |
| Glycine | 91 | 64 | 44 | 51 | 38 |
| Threonine | 43 | 37 | 24 | 19 | 3 |
| Valine | 52 | 37 | 48 | 24 | 4 |
| α-Alanine | 102 | 97 | 92 | 82 | 76 |
| β-Alanine | 95 | 87 | 85 | 85 | 83 |
| Citrulline | 95 | 107 | 48 | 38 | 38 |

As is evident from the data of the above Table, both α-alanine and β-alanine exhibit an excellent durable, stabilizing effect on secretin contained in the secretin preparations as compared with those of the others.

Experiment 2

Choice of buffer substance:

In the presence of several buffer substance hereinundermentioned, the stability of two secretin preparations prepared by lyophilization in accordance with the procedure of the preceding experiment was observed; one of the preparations contained 50 C.H.R. unit hormone activity of secretin and 20 mg of mannitol as the carrier, and the other contained 50 C.H.R. unit hormone activity of secretin and 20 mg of α-alanine as the carrier.

a. Effect of tartaric acid buffer (pH 4.5; C = 0.02 M) at 45°C.

| Carrier used | Remaining activity in C.H.R. Unit of secretin after | | |
|---|---|---|---|
| | 2 weeks | 4 weeks | 6 weeks |
| Mannitol | 86 | 79 | 66 |
| α-Alanine | 100 | 97 | 90 | b. Effect of phosphoric acid buffer (pH 4.5, C = 0.02 M) at 45°C.

| Carrier used | Remaining activity in C.H.R. Unit of secretin after | | |
|---|---|---|---|
| | 2 weeks | 4 weeks | 6 weeks |
| Mannitol | 76 | 61 | 0 |
| α-Alanine | 92 | 92 | 92 | c. Effect of succinic acid buffer (pH 4.5, C = 0.02 M) at 32°C.

| Carrier used | Remaining activity in C.H.R. Unit of secretin after | | |
|---|---|---|---|
| | 2 weeks | 4 weeks | 6 weeks |
| Mannitol | 85 | 72 | 67 |
| α-Alanine | 100 | 92 | 92 | d. Effect of citric acid buffer (pH 4.5, C = 0.02 M) at 45°C.

| Carrier used | Remaining activity in C.H.R. Unit of secretin after | | |
|---|---|---|---|
| | 2 weeks | 4 weeks | 6 weeks |
| Mannitol | 96 | 90 | 83 |

-continued

| Carrier used | Remaining activity in C.H.R. Unit of secretin after | | |
|---|---|---|---|
| | 2 weeks | 4 weeks | 6 weeks |
| α-Alanine | 100 | 100 | 93 | e. Effect of citric and phosphoric acid buffers (pH 4.5, C = 0.02 M) at 32°C.

| Carrier used | Remaining activity in C.H.R. Unit of secretin after weeks of | | | | | | | |
|---|---|---|---|---|---|---|---|---|
| | 2 | 4 | 6 | 8 | 10 | 13 | 16 | 18 |
| Mannitol | 101 | 92 | 100 | 90 | 0 | 0 | 0 | 0 |
| α-Alanine | 103 | 100 | 93 | 101 | 106 | 100 | 97 | 99 | f. Effect of citric and phosphoric acid buffers (pH 4.5, C = 0.02 M) at 45°C.

| Carrier used | Remaining activity in C.H.R. Unit of secretin after weeks of | | | | | | | |
|---|---|---|---|---|---|---|---|---|
| | 2 | 4 | 6 | 8 | 10 | 13 | 16 | 18 |
| Mannitol | 86 | 80 | 35 | 10 | 0 | 0 | 0 | 0 |
| α-Alanine | 95 | 94 | 98 | 99 | 87 | 98 | 89 | 96 |

The above data show that under the severe thermal treatment, the lyophilized secretin composition which contains mannitol as the carrier rapidly loses its secretin activity and that the lyophilized secretin composition which contains α-alanine as the carrier maintains its secretin activity for a prolonged period of storage.

It may thus be said that alanine, especially α-alanine, is a preferable carrier for the production of secretin preparations by lyophilization of its aqueous solution.

The present invention will be illustrated by the following Examples.

EXAMPLE 1

An aqueous solution was prepared by dissolving under sterilization 2 grams of α-alanine and 5000 Crick, Harper and Raper units of secretin into 50 ml of a buffer solution of pH 4.5 containing 0.03 M citric and phosphoric acids. Each 0.5 ml aliquot of the resulting solution was lyophilized in an ampoule of 2 ml capacity and then sealed.

EXAMPLE 2

An aqueous solution was prepared by dissolving under sterilization 3 grams of β-alanine and 5000 Crick, Harper and Raper units of secretin into 50 ml of a 0.02 M tartaric acid buffer solution of pH 4.5. Each 0.5 ml aliquot of the resulting solution was lyophilized in an ampoule of 2 ml capacity and then sealed.

EXAMPLE 3

An aqueous solution was prepared by dissolving under sterilization 1 gram of α-alanine, 1 gram of β-alanine and 5000 Crick, Harper and Raper units of secretin into 50 ml of a 0.02 M citric acid buffer solution at pH 5.0. Each 0.5 ml aliquot of the resulting solution was lyophilized in an ampoule of 2 ml capacity and then sealed.

What is claimed is:

1. A process for producing a stabilized powdery secretin preparation which comprises lyophilizing an aqueous solution of secretin having a pH of 4–7 in the presence of a 2–10% aqueous solution of alanine as carrier for the secretin.

2. A process as claimed in claim 1, wherein the alanine is a member selected from the group consisting of α-alanine, β-alanine and mixtures thereof.

3. A process as claimed in claim 2, wherein the lyophilization is carried out in the presence of a buffer selected from the group consisting of tartaric acid, phosphoric acid, succinic acid and citric acid.

4. A pharmaceutical composition consisting essentially of a minor proportion of secretin and a major proportion of a member selected from the group consisting of α-alanine, β-alanine and mixtures thereof as carrier therefor.

5. A pharmaceutical composition consisting essentially of a minor proportion of secretin, a member selected from the group consisting of α-alanine, β-alanine and mixtures thereof as carrier therefor and a buffer selected from the group consisting of tartaric acid, phosphoric acid, succinic acid and citric acid in an amount sufficient to impart a pH of 4–7 to an aqueous solution of said composition.

* * * * *